US012312573B1

United States Patent
Diller et al.

(10) Patent No.: US 12,312,573 B1
(45) Date of Patent: May 27, 2025

(54) TISSUE CULTURE PLATE MATERIAL RETAINER SYSTEM

(71) Applicant: Amnio Technology LLC, Phoenix, AZ (US)

(72) Inventors: Robert B. Diller, Phoenix, AZ (US); Audrey Arvonen, Mesa, AZ (US); Chad Hagenbuch, Mesa, AZ (US)

(73) Assignee: Amnio Technology LLC, Phoenix, AZ (US)

( * ) Notice: Subject to any disclaimer, the term of this patent is extended or adjusted under 35 U.S.C. 154(b) by 0 days.

(21) Appl. No.: 18/918,990

(22) Filed: Oct. 17, 2024

(51) Int. Cl.
*C12M 3/00* (2006.01)
*C12M 1/00* (2006.01)
*C12M 1/12* (2006.01)

(52) U.S. Cl.
CPC .................................. *C12M 25/04* (2013.01)

(58) Field of Classification Search
CPC ............................. C12M 23/12; C12M 25/04
See application file for complete search history.

(56) References Cited

U.S. PATENT DOCUMENTS

| | | | |
|---|---|---|---|
| 3,649,464 A | 3/1972 | Freeman | |
| 5,272,083 A * | 12/1993 | Butz | C12M 25/04 435/297.5 |
| 5,321,955 A | 6/1994 | Leonard | |
| 5,536,662 A * | 7/1996 | Humphries | C12M 25/04 435/287.4 |
| 7,188,734 B2 * | 3/2007 | Konrad | G01N 33/491 422/561 |
| 7,257,953 B2 | 8/2007 | Rada | |
| 7,981,668 B2 * | 7/2011 | Wilkes | C12M 25/04 435/297.5 |
| 11,709,160 B2 | 7/2023 | Hickerson et al. | |
| 2008/0009027 A1 | 1/2008 | Fraker et al. | |
| 2008/0076170 A1 * | 3/2008 | Annala | C12M 25/04 435/305.1 |
| 2008/0194017 A1 * | 8/2008 | Esser | C12M 23/12 435/307.1 |
| 2019/0185801 A1 | 6/2019 | Frank et al. | |
| 2021/0346850 A1 | 11/2021 | Young et al. | |
| 2024/0174960 A1 | 5/2024 | Maccione et al. | |

* cited by examiner

*Primary Examiner* — Nathan A Bowers
(74) *Attorney, Agent, or Firm* — Invention To Patent Services; Alex Hobson

(57) ABSTRACT

A tissue culture plate material retainer system includes a culture material retainer having a retainer ring with a retainer ring gap to enable the retainer ring to be compressed for insertion into a culture plate well and a plurality of retainer legs that extend down from the retainer ring to hold culture material down in the well of the culture plate in or under a culture medium. A culture material retainer has a retainer ring that extends along a top and a plurality of retainer legs that extend down from the retainer ring. The retainer ring extends from a first end to a second end forming a retainer ring gap that enables the retainer ring and culture material retainer to collapse or flex radially inward for insertion into a wall.

19 Claims, 3 Drawing Sheets

TISSUE CULTURE PLATE MATERIAL RETAINER SYSTEM

BACKGROUND OF THE INVENTION

Field of the Invention

The invention relates to a tissue culture plate material retainer system including a material retainer having a retainer ring with a retainer ring gap to enable the retainer ring to be compressed for insertion into a culture plate well and a plurality of retainer legs that extend down from the retainer ring to hold culture material down in the well of the culture plate.

Background

Culture material is typically placed in a well of a tissue culture plate and a culture medium, a fluid, is added to the well. In some cases, the culture material has a density less than the fluid and floats. This may prevent the culture material from making contact with the culture medium and may affect cell culture studies by producing inconsistent results.

SUMMARY OF THE INVENTION

The invention is directed to a tissue culture plate material retainer system including a culture material retainer having a retainer ring with a retainer ring gap to enable the retainer ring to be compressed for insertion into a culture plate well and a plurality of retainer legs that extend down from the retainer ring to hold culture material down in the well of the culture plate.

An exemplary culture material retainer has a retainer ring that extends along a top of the culture material retainer and a plurality of retainer legs that extend down from the retainer ring. The retainer ring extends in an arc having an outer diameter or radius of curvature from a first end to a second end forming a retainer ring gap that enables the retainer ring to be compressed or collapsed radially inward for insertion into a well of a culture plate. The retainer ring may extend in an arc that is slightly larger than the opening of the culture plate well, wherein the outer diameter of the retainer ring is a percentage larger than the diameter of the top of the culture plate well, such as about 3% or more, about 5% or more, about 7% or more about 10% or more, about 15% or more and any range between and including the percentages provided. The culture material retainer and the retainer ring may be constricted or synched to reduce the diameter of the retainer ring for insertion into the culture plate well, wherein the first end of the retainer ring is move toward the second end of the retainer ring to reduce the retainer ring gap dimension.

A retainer leg may extend from the first end and/or the second end of the retainer ring to an extended end. A culture material retainer may have two, three, four, five, six or more retainer legs although three or four retainer legs generally preferred as this number is effective for holding down culture material.

A retainer leg(s) may have retainer feet extending radially inward from the extended end of the retainer leg. A retainer foot may extend radially inward and form a foot diameter along the most radially inward surface of the retainer foot and this foot diameter may be less than the retainer ring diameter.

Retainer legs may extend a leg offset angle from the retainer ring such that the outermost portion of the extended end of the retainer legs are radially inward from the outermost portion of the retainer ring. This enables easier alignment and insertion of the culture material retainer into a well of a culture plate.

A leg connector may extend between adjacent legs and may for a leg ring. A leg ring may form a planar base for contact with a culture material. A leg ring may also extend from a first retainer leg extending most proximal to a first end of the retainer ring to a second retainer leg extending most proximal to a second end of the retainer ring. The leg ring may therefore form a leg ring gap that also aids in compression of the culture material retainer for insertion into a well. A base of the culture material retainer may have protrusions to allow culture medium to flow between the culture material retainer and the culture material and these protrusions may be ridges that may preferably extend linearly from an outside to an inside of the base or dome shapes protrusions.

A culture material retainer may be a monolith being made from a single contiguous material, such as a plastic that may be a molded plastic part.

The summary of the invention is provided as a general introduction to some of the embodiments of the invention and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
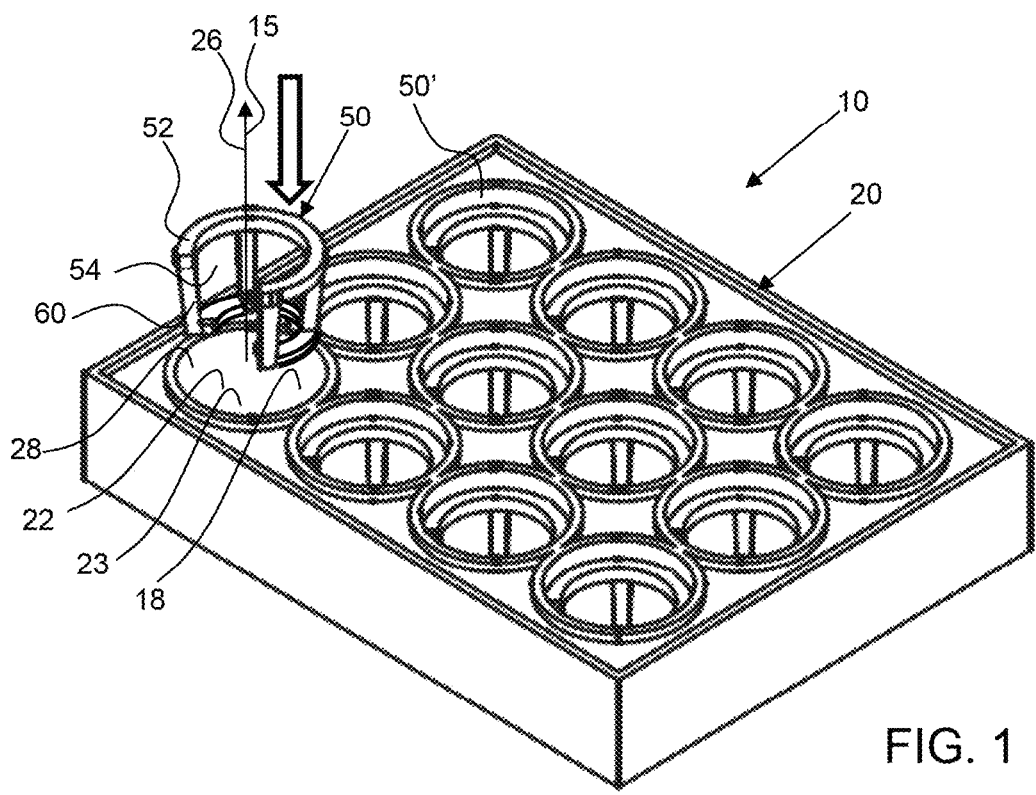
FIG. 1 shows a perspective view of a culture plate culture material retainer system including a culture plate with a plurality of wells and a plurality of culture material retainers inserted into the wells and one culture material retainer being inserted into a well.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purpose of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 2:
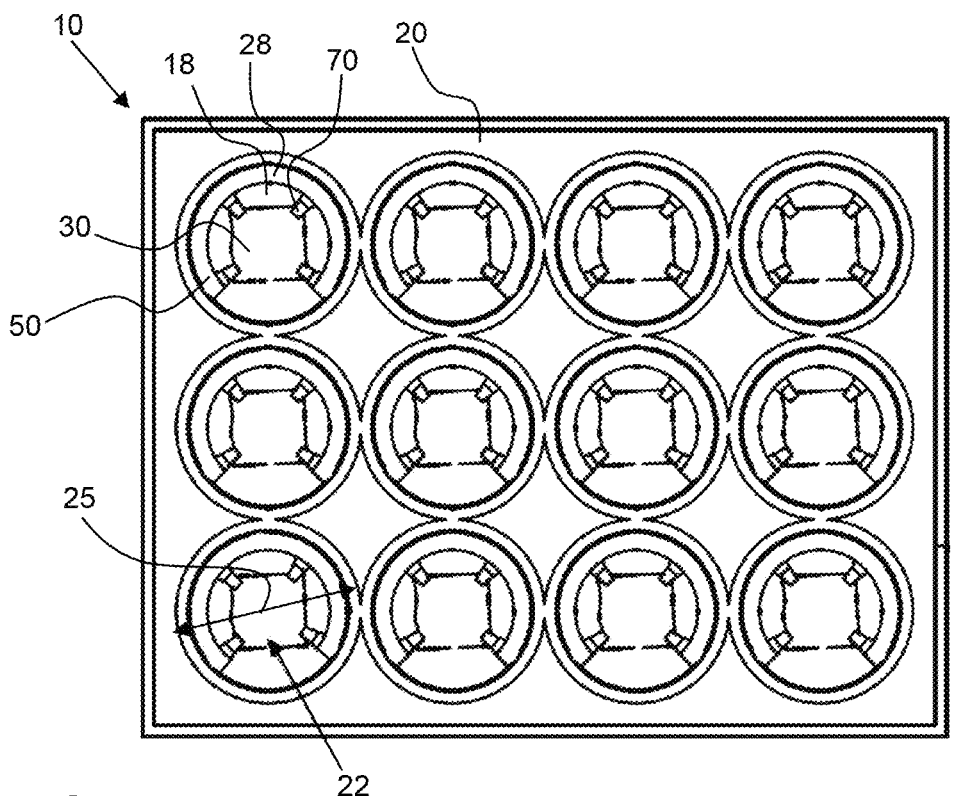
FIG. 2 shows a top view of a cell culture plate culture material retainer system including a culture plate with a plurality of wells and culture material retainers inserted therein.

Referring now to FIGS. 1 and 2, a culture plate culture material retainer system 10 includes a culture plate 20 with a plurality of wells 22 and culture material retainers 50, 50'. The tissue culture material retainer 50 is configured to slide down into the well 22 of culture plate 20 as indicated by the bold arrow. The culture material retainer 50 has a retainer ring 52 and a plurality of retainer legs 60 that extend down into the well to hold down a culture material 30 therein. The insert opening 23 of the well 22 is smaller in diameter than the diameter of the retainer ring 52 and the retainer ring gap 54 allows the retainer ring to compress or cinch upon insertion into the well to enable the retainer ring and culture material retainer 50 to fit within the well 22. Compressing or cinching the retainer ring during insertion into the well produces a stored force that causes the retainer ring to press outward onto the interior wall 28 of the well to retain the culture material retainer 50 within the well. The culture material retainer is inserted along the well axis 26 into the well. The well axis may be a vertical axis 15 when the culture plate 20 is resting on a horizontal surface. A culture medium 18, such as a fluid may be configured within the well 22 and the retainer legs may extend through the culture medium 18 to contact the culture material 30. A culture medium may include a composition to promote cell growth and may include glucose, amino acids, a serum and the like. A culture material may be a biological material, such as tissue or may be a bioresorbable material, and may be a synthetic material including a polymer or polymers. A culture material is any material or substrate utilized for cells to grow onto or into. A culture material may be a biocompatible material. A culture material may be a flat planar sheet of material that has two planar opposing surfaces and may have a density that is less than the density of the culture medium, which may cause the culture material to float. The culture material retainer may retain the culture material down in the culture medium.

Referring now to FIGS. 3 to 6, a culture material retainer 50 has a retainer ring 52 that extends from a first end 53 to a second end 55 to form a retainer ring gap 54 therebetween. The retainer ring may be disc shaped having a thickness 505 (shown in FIG. 6) of about 25 mm or less, about 20 mm or less, about 15 mm or less, about 10 mm or less and any range between and including the thickness values provided. A thin retainer ring may enable easier squeezing of the culture material retainer 50 for insertion into the well of the culture plate. The retainer ring may be a disc ring with a retainer ring gap. A thin retainer ring may be easier to compress for insertion into a wall. This retainer ring gap 54 enables the retainer ring 52 to collapse or cinch inward to reduce an outer diameter 58 of the retainer ring for insertion into the well of the culture plate. The retainer ring extends in an arc from the first end to the second end and has a width from the outer diameter 58 to the inner diameter 581, shown in FIG. 4. The width may be about 3 mm or more, about 5 mm or more, about 7.5 mm or more, about 10 mm or more, about 15 mm or more, about 20 mm or more and any range between and including the width values provided. The retainer ring then pushes outward on the interior wall of the well to retain the culture material retainer in the well. The retainer ring gap 54 may extend a retainer ring retainer degree 57 such as about 10 degrees or more, about 20 degrees or more about 30 degrees or more, about 45 degrees or more, about 60 degrees or more, about 90 degrees or more, about 120 degrees or more and any range between and including the retainer ring gap degrees provided.

Figures 3, 4, 5:
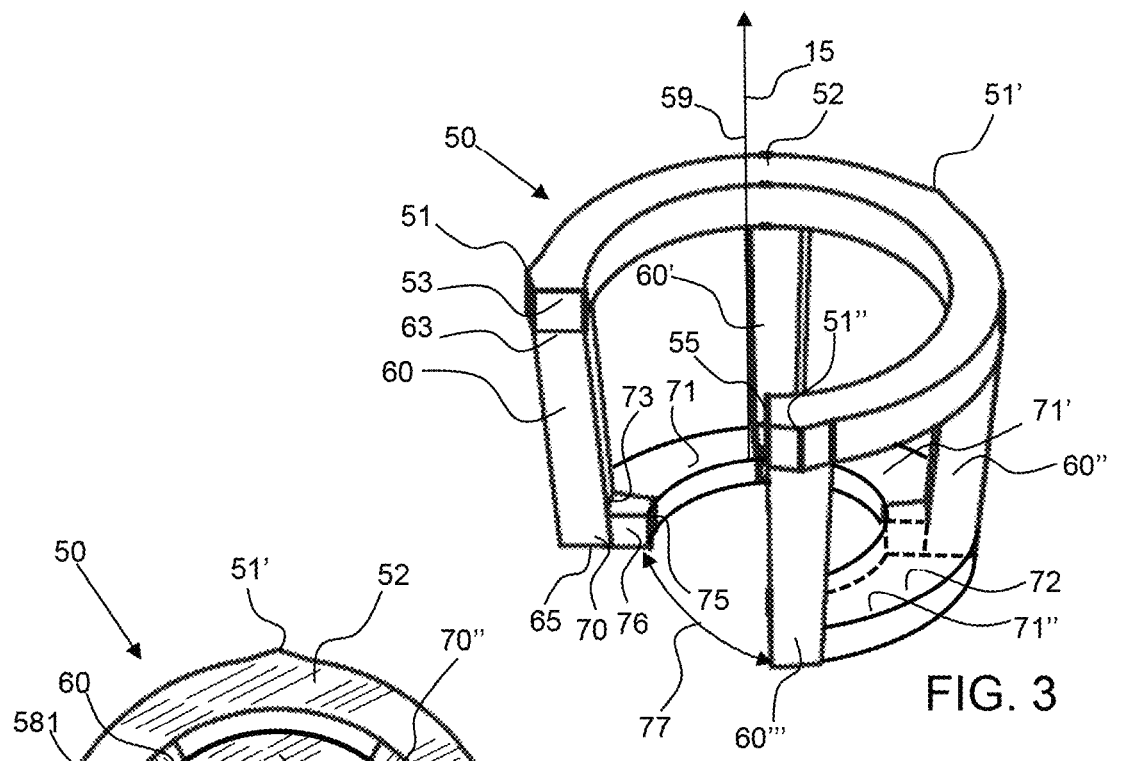
FIG. 3 shows a top side perspective view a culture material retainer having a retainer ring that extends from a first end to a second end to form a retainer ring gap therebetween and four retainer legs that extend from the retainer ring to a leg extended end having a leg foot and a leg foot extension extending radially inward toward a centerline of the culture material retainer.
FIG. 4 shows a top view of the culture material retainer shown in FIG. 3.
FIG. 5 shows a bottom perspective view of the culture material retainer shown in FIG. 3.
Figure 6:
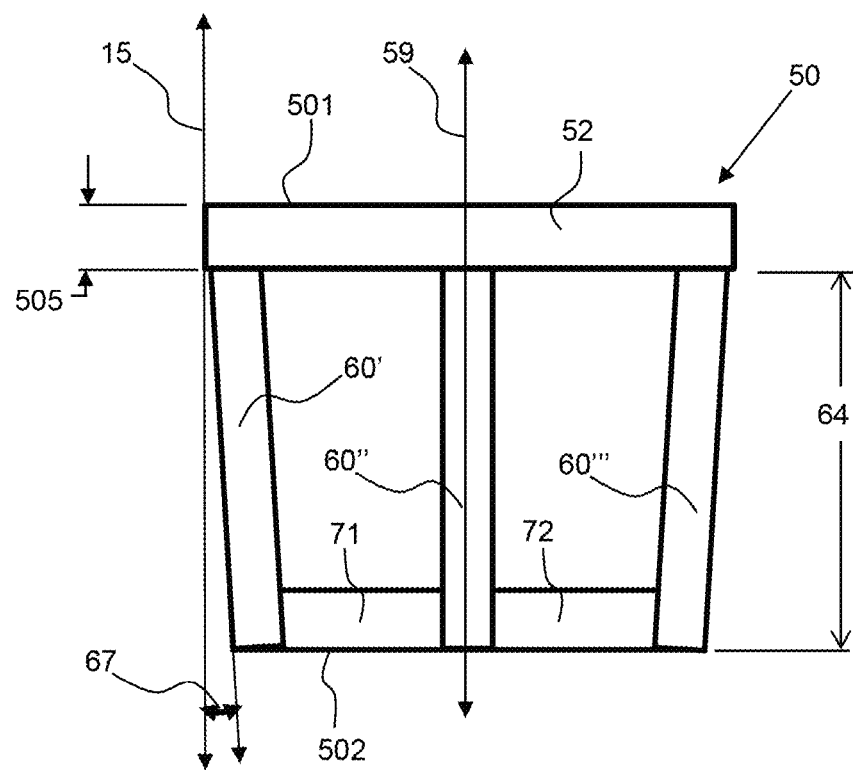
FIG. 6 shows a side view of an exemplary culture material retainer having legs that extend a leg offset angle from a vertical axis 15, or a centerline axis of the culture material retainer.

The culture material retainer 50 has four retainer legs 60, 60', 60", 60"' that extend from the retainer ring to a leg extended end 65 that may have a leg foot 70 configured on the extended end. A leg foot may have a foot connected end 73, connected with the retainer leg 60 and a foot extended end 75, as shown in FIG. 3. A leg or legs may extend from the first end 53 and second end 55 of the retainer ring 52 as shown and this may provide some additional stability to the retainer ring and culture material retainer 50, especially in the vertical axis 15 or along the centerline 59. A leg foot may include a leg foot extension 76 may extend radially inward from the leg extended end 65 toward a centerline 59 of the culture material retainer 50 to the foot extended end. Each retainer leg 60 has a leg connected end 63, connected with the retainer ring, and a leg extended end 65, which may have a leg foot 70, configured to retain the culture material within the well of a culture plate. The legs extend a leg length 64 from said leg connected end 63 to the leg extended end 65 as shown in FIG. 6. Each leg may have a leg width 69, shown in FIG. 5 that may taper from the leg connected end 63 to the leg extended end 65. A leg width may be measured as degree about the circumference of the retainer ring or by a straight line measurement orthogonal to the centerline axis and may be no more than about 35 degrees, no more than about 30 degrees, no more than about 25 degrees, no more than about 20 degrees, no more than about 15 degrees and any range between and including the values provided, or no more than about 25 mm, no more than about 20 mm, no more than about 15 mm, no more than about 10 mm, no more than about 5 mm and any range between and including the values provided. It may be desirable that the legs not be too wide as this may make it difficult to flex the culture media retainer 50 for insertion into the well of the culture tray.

Each leg may extend at a leg offset angle 67, shown in FIG. 6, to place the leg extended end radially inward from the outer diameter 58 of the retainer ring. This may make it easier to insert the culture material retainer 50 into a well. The leg offset angle may be about 5 degrees or more, about 10 degrees or more, about 15 degrees or more, about 20 degrees or more, about 25 degrees or more, about 30 degrees or less and any range between and including the values provided. As shown in FIG. 4, the leg extended end may be configured along a leg extended diameter 68 that may be less than the outer diameter 58 of the retainer ring. Also, the leg feet extension may extend radially inward toward the centerline 59 of the culture material retainer 50 to form a foot inner diameter 78 that is smaller than both the leg extended diameter 68 and retainer ring outer diameter 58.

A leg connector 71, 71', 71'' may extend between adjacent retainer legs or between the leg feet and this may form a leg ring 72, a continuous ring from a first leg 60 on a first side of the retainer ring gap 54 to a fourth leg 60''' on a second and opposing side of the retainer ring gap 54. The leg ring 72 forms a leg ring gap 77 that as shown is in alignment with the retainer ring gap 54. A leg ring gap 77 may extend the same degree as the retainer ring gap 57, shown in FIG. 4. A leg connector 71 or leg ring 72 may extend in a plane with the leg extended end 65 and/or the leg foot 70 or leg foot extension, as best shown in FIG. 5. This planar surface holds a culture material down within the well in a uniform manner. Protrusions 87 may extend from the base 502 of the culture material retainer 50 such as from the leg foot 70, leg foot extension 76 and/or the leg connector 71, which may form the leg ring 72 to enable culture medium to flow under the base 502 and along the culture material. These protrusions may be dome shaped, or ridges that extend from an outside circumference to an inside circumference or radius of the base 502. A single protrusion is shown in FIG. 5 for clarity, but a base may include a plurality of protrusions of the leg feet or along the leg ring base.

Figure 7:
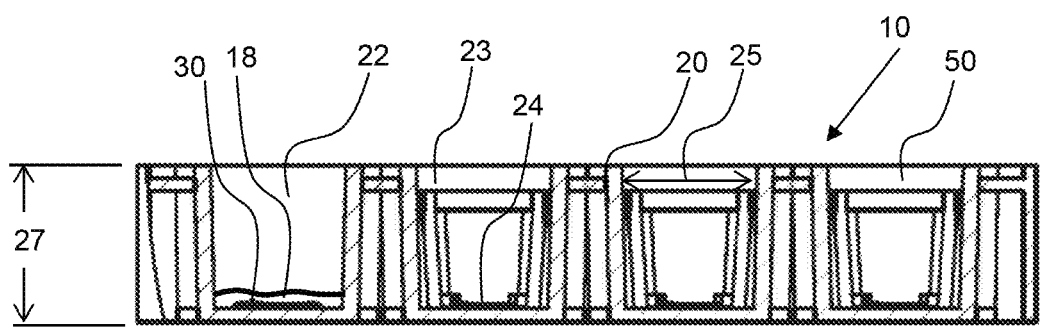
FIG. 7 shows a cross-sectional view of an exemplary culture plate culture material retainer system including a culture plate with a plurality of wells and culture material retainers.

The culture material retainer 50 has a height 503 from the top 501 to the base 502 as shown in FIG. 5. This height may be slightly less than a depth 27 of a well as shown in FIG. 7, to enable the culture material retainer 50 to fit within the well with the retainer ring 52 resting along the inside wall of the well with the feet holding the culture material down in the bottom of the well. The retainer ring 52 may have ring retainer protrusions 51, 51', 51'', best shown in FIG. 4, that protrude radially outward from the retainer ring, or radially out from the centerline 59 of the culture material retainer 50. These ring retainer protrusions may be uniformly positioned around the outer circumference or perimeter of the retainer ring. As shown, there are three ring retainer protrusions that are configured less than 180 degrees apart. There may be four ring retainer protrusions, and these may positioned about the outer perimeter less than 120 degrees apart. It may be desirable to have ring retainer protrusions configured proximal to the first end 53 and second end 55 of the retainer ring as this may be where the highest stored force is applied on the interior wall of the well. These end ring retainer protrusions may be positioned 10 mm or less or even 5 mm or 3 mm or less from the end of the retainer ring, or put another way, no more than about 20 or no more than about 10 degrees from the end of the retainer ring.

As best shown in FIG. 5, a leg foot has a length 74 from outer perimeter or circumference of the extended end of the retainer leg, or leg foot 70 to the inner circumference or perimeter of the leg foot or leg foot extension 76 that terminates at the foot extended end 75, as shown in FIG. 5. As described herein, the leg foot extension extends radially inward toward a centerline 59 of the retainer ring 50. The leg foot width may be a portion of the retainer ring diameter, such as no more than about 35%, no more than about 25%, no more than about 10% no more than about 5% and any range between and including the percentages provided.

A culture material retainer 50 may be a monolith, made from a single material, such as plastic. A monolithic culture material retainer 50 may be made by molding, such as injection molding and may be made of plastic.

As shown in FIG. 7, the culture material retainer 50 extends into the well 22 having a well depth 27 from an insert opening 23 to a base 24. The insert opening 23 has an insert well diameter 25 that is smaller than the retainer ring diameter or diameter formed by the outermost portion of the retainer ring, including the ring retainer protrusions. The legs and leg feet of the culture material retainer 50 touch and hold the culture material 30 down in the well 22 of the culture plate and submerged in culture medium 18.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A tissue culture plate material retainer system comprising:
   a) a tissue culture plate comprising a well having an insert opening having an insert opening diameter, a base and a depth from said insert opening to said base;
   b) a material configured in the base of said well;
   c) material retainer comprising:
      i) a retainer ring extending from a first end to a second end;
      ii) a retainer ring gap extending a ring gap degree of at least 10 degrees between the first end and the second end of the retainer ring;
   wherein the retainer ring has a retainer ring diameter greater than the insert diameter of said well;
   wherein the retainer ring gap enables compression of the retainer ring to reduce said retainer ring diameter for insertion of the retainer ring into the insert opening of the well; and
      iii) a plurality of retainer legs each extending from a leg connected end, connected to the retainer ring to an extended end of the retainer leg that holds said material against the base of the well; and
   wherein at least a portion of the plurality of retainer legs further comprises a lea foot having a leg foot extension that extends radially inward from said extended end of the retainer leg to a foot extended end.

2. The tissue culture plate material retainer system of claim 1, wherein the plurality of retainer legs includes at least three retainer legs.

3. The tissue culture plate material retainer system of claim 1, wherein the plurality of retainer legs includes at least four retainer legs.

4. The tissue culture plate material retainer system of claim 1, wherein the leg feet extend a foot diameter that is less than retainer ring diameter.

5. The tissue culture plate material retainer system of claim 1, wherein foot diameter is at least 10% less than the retainer ring diameter.

6. The tissue culture plate material retainer system of claim 1, wherein the leg feet have a length that is 35% or less of the retainer ring diameter.

7. The tissue culture plate material retainer system of claim 1, further comprising a leg connector extending between adjacent leg feet.

8. The tissue culture plate material retainer system of claim 1, further comprising a leg ring extending along a base of the culture material retainer and coupled to each of the extended ends of the plurality of retainer legs.

9. The tissue culture plate material retainer system of claim 8, wherein the leg ring forms a leg ring gap between two of the adjacent retainer legs of said plurality of retainer legs.

10. The tissue culture plate material retainer system of claim 1, wherein the retainer legs extend at a leg offset angle from the retainer ring that is at least 5 degrees.

11. The tissue culture plate material retainer system of claim 1, wherein the retainer ring further comprises a ring retainer protrusion extending radially outward from the retainer ring.

12. The tissue culture plate material retainer system of claim 1, wherein the retainer legs extend at a leg offset angle from the retainer ring that is at least 5 degrees.

13. The tissue culture plate material retainer system of claim 1, wherein the culture material retainer is a monolith.

14. The tissue culture plate material retainer system of claim 1, further comprising a leg connector extending between adjacent leg feet.

15. The tissue culture plate material retainer system of claim 14, further comprising a leg ring extending along a base of the culture material retainer and coupled to each extended end of the plurality of retainer legs.

16. The tissue culture plate material retainer system of claim 15, wherein the leg ring forms a leg ring gap between two of the adjacent retainer legs of said plurality of retainer legs.

17. The tissue culture plate material retainer system of claim 16, wherein the retainer ring further comprises a ring retainer protrusion configured no more than 20 degrees from each of the first end and second end of the retainer ring, and wherein each ring retainer protrusion extends radially outward from the retainer ring.

18. The tissue culture plate material retainer system of claim 1, wherein the retainer ring further comprises a ring retainer protrusion extending radially outward from the retainer ring.

19. The tissue culture plate material retainer system of claim 1, wherein each of the plurality of legs extend no more than 20 degrees around the retainer ring.

* * * * *